(12) United States Patent
Yang et al.

(10) Patent No.: US 10,548,862 B2
(45) Date of Patent: Feb. 4, 2020

(54) TOPICAL FORMULATION AND METHOD FOR PREVENTING OR TREATING ACNE

(71) Applicants: Lester J. Wu, Flushing, NY (US); Gongwin Biopharm Holdings Co., Ltd., Grand Cayman (KY)

(72) Inventors: Chuan-Ching Yang, Taipei (TW); Mao-Yuan Lin, Taipei (TW); Tai-Jung Wu, Taipei (TW); Chi-Chiang Tu, Taipei (TW); Shun-Chi Wu, Taipei (TW)

(73) Assignees: Lester J. Wu, Flushing, NY (US); Gongwin Biopharm Holdings Co., Ltd., Grand Cayman (KY)

( * ) Notice: Subject to any disclaimer, the term of this patent is extended or adjusted under 35 U.S.C. 154(b) by 0 days.

(21) Appl. No.: 15/858,617

(22) Filed: Dec. 29, 2017

(65) Prior Publication Data

US 2019/0201356 A1 Jul. 4, 2019

(51) Int. Cl.
| | |
|---|---|
| A61K 31/18 | (2006.01) |
| A61K 9/00 | (2006.01) |
| A61K 47/20 | (2006.01) |
| A61K 47/34 | (2017.01) |
| A61K 47/10 | (2017.01) |
| A61K 47/40 | (2006.01) |
| A61P 17/10 | (2006.01) |

(52) U.S. Cl.
CPC ............ *A61K 31/18* (2013.01); *A61K 9/0014* (2013.01); *A61K 47/10* (2013.01); *A61K 47/20* (2013.01); *A61K 47/34* (2013.01); *A61K 47/40* (2013.01); *A61P 17/10* (2018.01)

(58) Field of Classification Search
None
See application file for complete search history.

(56) References Cited

U.S. PATENT DOCUMENTS

| | | | | |
|---|---|---|---|---|
| 4,657,901 A | * | 4/1987 | Ueda | A61K 31/565 514/171 |
| 4,699,924 A | * | 10/1987 | Durrant | A61K 8/365 514/558 |
| 2018/0170869 A1 | * | 6/2018 | Musicki | C07C 381/10 |

FOREIGN PATENT DOCUMENTS

| | | | |
|---|---|---|---|
| WO | WO2014/140861 | * | 9/2014 |
| WO | WO 2016/097389 | * | 6/2016 |

OTHER PUBLICATIONS

Bhatia et al. Propionibacterium Acnes and Chronic Diseases—The Etiology of Chronic Diseases—NCBI Bookshelf. Washington (DC): National Academies Press (US); 2004 (https://www.ncbi.njm.nih.gov/books/NBK83685/). (Year: 2004).*

Goodman and Gilman's The Pharmacological Basis of Therapeutics (Tenth Edition (2001), McGraw Hill, Chapter I, pp. 3-29). (Year: 2001).*

J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*

* cited by examiner

*Primary Examiner* — Dennis Heyer
(74) *Attorney, Agent, or Firm* — Mintz Levin Cohn Ferris Glvosky and Popeo, P.C.; Peter F. Corless; Joohee Lee

(57) ABSTRACT

Provided is a topical formulation for preventing or treating acne, including a benzenesulfonamide derivative, and a pharmaceutically or cosmetically acceptable excipient. Also provided is a method for preventing or treating acne, including applying the topical formulation on skin of a subject in need thereof.

10 Claims, 10 Drawing Sheets

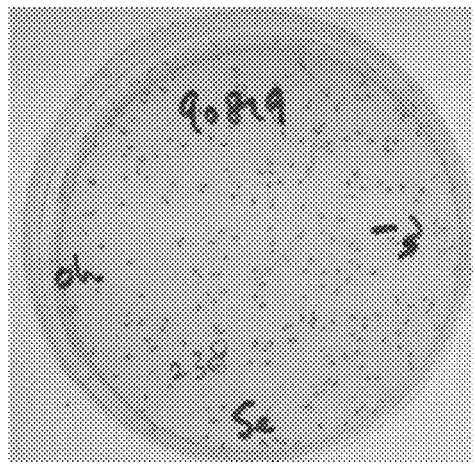
(Group 1, 0 hour)
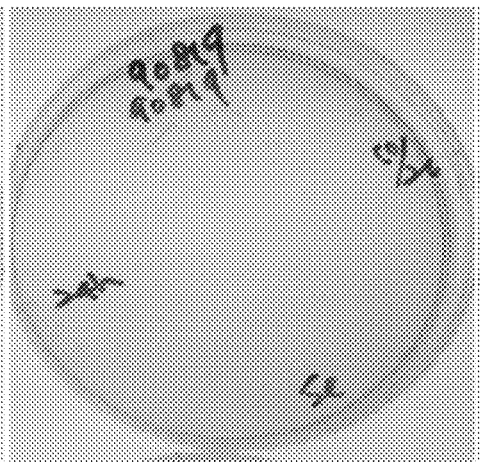
(Group 1, 24 hours)
FIG. 2A      FIG. 2B
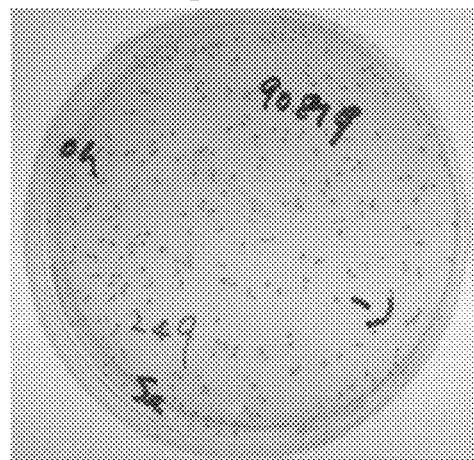
(Group 2, 0 hour)
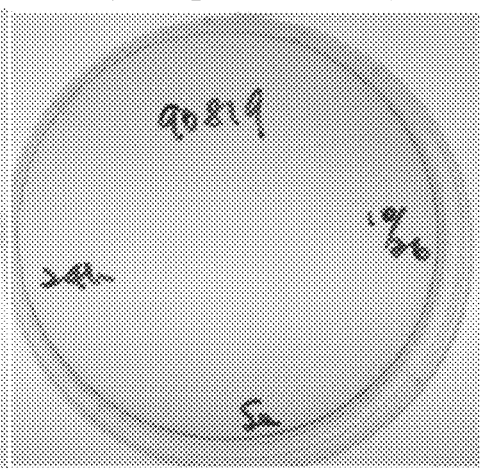
(Group 2, 24 hours)
FIG. 2C      FIG. 2D (Group 1, 0 hour)  (Group 1, 24 hours)
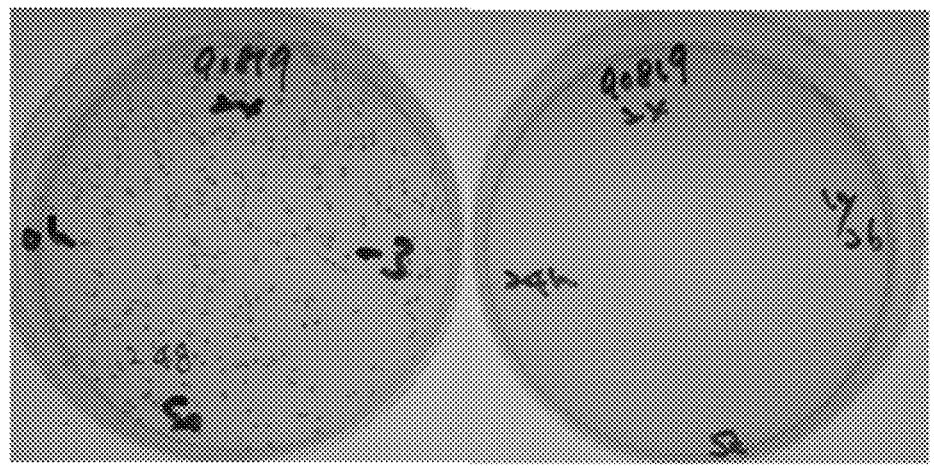
FIG. 3A          FIG. 3B
(Group 2, 0 hour)  (Group 2, 24 hours)
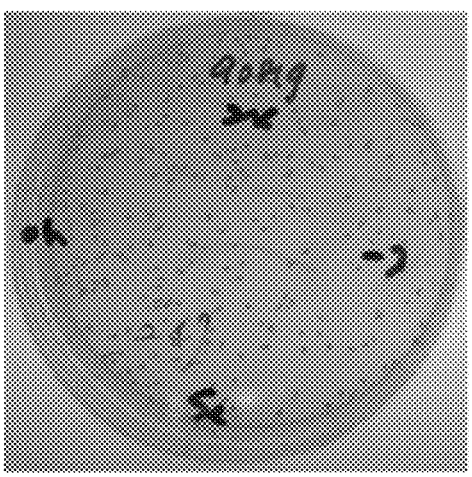 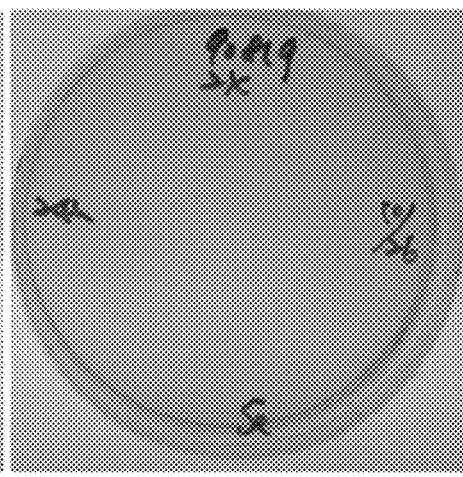
FIG. 3C          FIG. 3D (Group 1, 0 hour)      (Group 1, 24 hours)
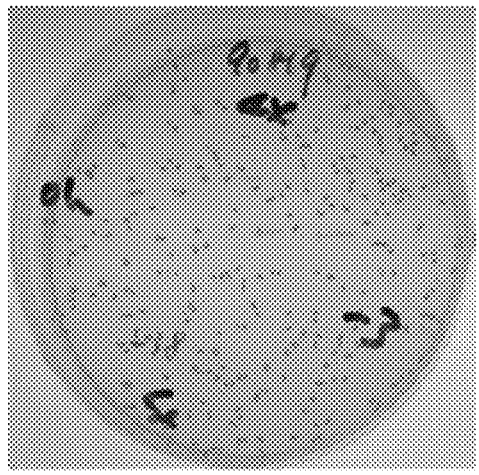 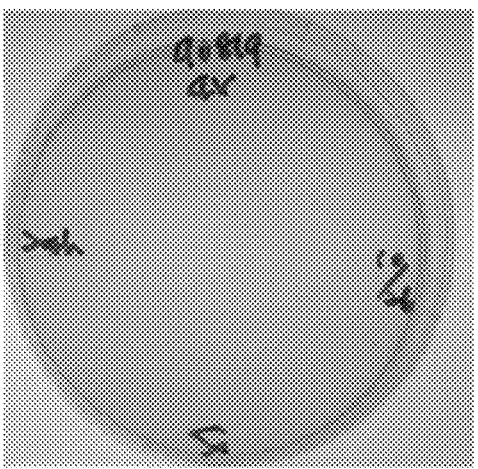
FIG. 4A      FIG. 4B
(Group 2, 0 hour)      (Group 2, 24 hours)
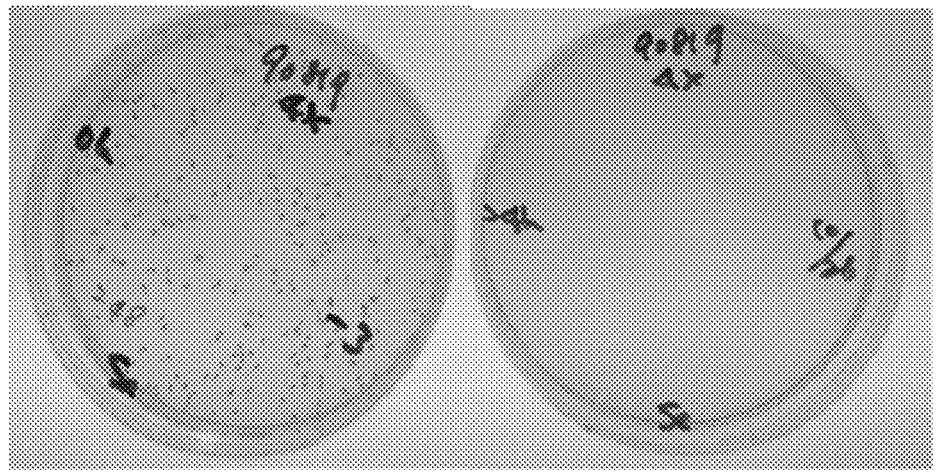
FIG. 4C      FIG. 4D (Group 1, 0 hour)

(Group 1, 24 hours)

(Group 2, 0 hour)     (Group 2, 24 hours)

(Group 1, 0 hour) (Group 1, 24 hours)
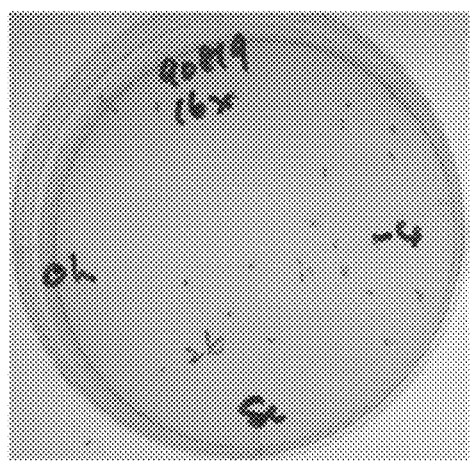 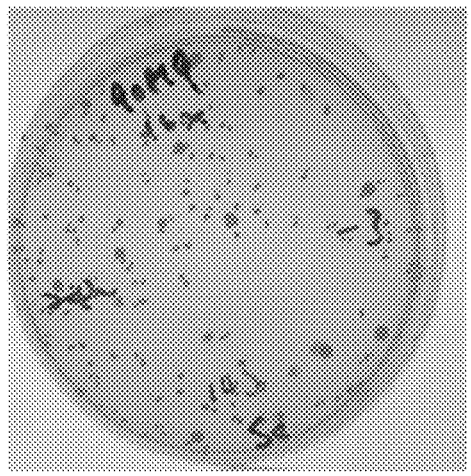
FIG. 6A   FIG. 6B
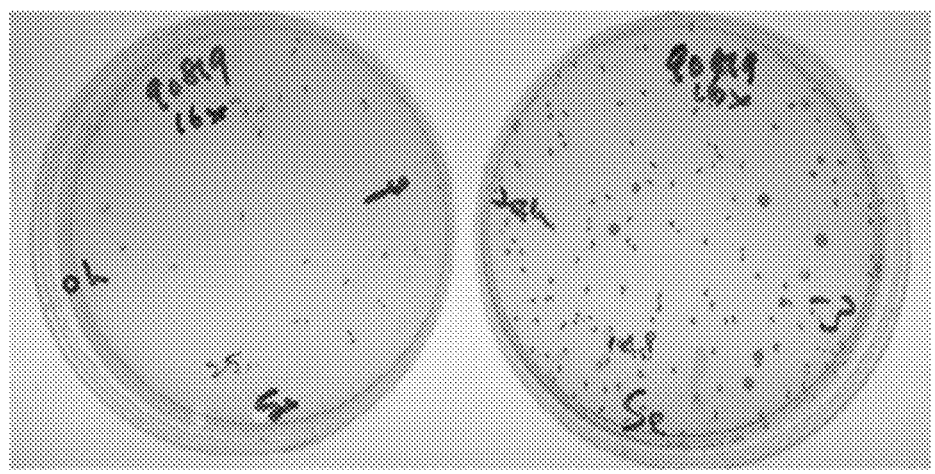
FIG. 6C   FIG. 6D

TOPICAL FORMULATION AND METHOD FOR PREVENTING OR TREATING ACNE

BACKGROUND

1. Technical Field

The present disclosure relates to a topical formulation, and particularly to a topical formulation for preventing or treating acne. The present disclosure also relates to a method for preventing or treating acne by applying the topical formulation to skin of a subject in need thereof.

2. Description of Associated Art

Acne is a skin disease and is considered as a chronic inflammation of hair follicles and oil glands, which usually occurs on the face, back, chest, shoulders and arms. Acne affects males and females at any age but occurs more frequently in the teenagers due to hormonal changes, improper skin cleaning or dietary triggers. The increased hormone would block pore and irritate hair follicles, and once improperly cleaning face, acne-associated bacteria would grow within the blocked pores, followed by causing more inflammation redness and pustules.

Topical agents for acne treatment include topical retinoid, benzoyl peroxide (BPO), topical antimicrobial agents such as clindamycin, erythromycin, fusidic acid, and azelaic acid. Even providing antimicrobial and anti-inflammation effects against acne, the topical agents have some drawbacks. For example, the topical retinoid may cause dry skin, burning sensation, irritation and photosensitivity; the BPO may cause strong irritation; the topical antimicrobial agents provide less antimicrobial and anti-inflammation effects when used alone, and thus usually suggested to be used in combination with the topical retinoid or BPO; and azelaic acid may also cause skin irritation.

Therefore, developing a topical agent which provides strong antimicrobial and anti-inflammation effects for acne treatment without causing adverse effects is an urgent problem to be solved in the art.

SUMMARY

The present disclosure is based, at least in part, on the discovery that a topical formulation comprising a benzenesulfonamide derivative has anti-acne effects as well antimicrobial activity. The anti-acne effects are from direct action against the bacteria on the skin that are known to cause acne.

The topical formulation for preventing or treating acne provided in the present disclosure comprises a benzenesulfonamide derivative, and a pharmaceutically or cosmetically acceptable excipient thereof.

In one embodiment of the present disclosure, the benzenesulfonamide derivative in the topical formulation may be represented by following formula (I):

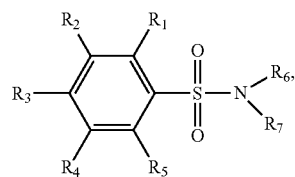

(I)

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and wherein the alkyl, alkoxy, cycloalkyl, cycloheteroalkyl group and the ring are unsubstituted or substituted with one or more substituents. In one embodiment of the present disclosure, the substituent may be selected from the group consisting of phenyl, halo, oxo, ether, hydroxyl, carboxyl, amino, sulfo and sulfonamide group.

In one embodiment of the present disclosure, the benzenesulfonamide derivative may be selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide,

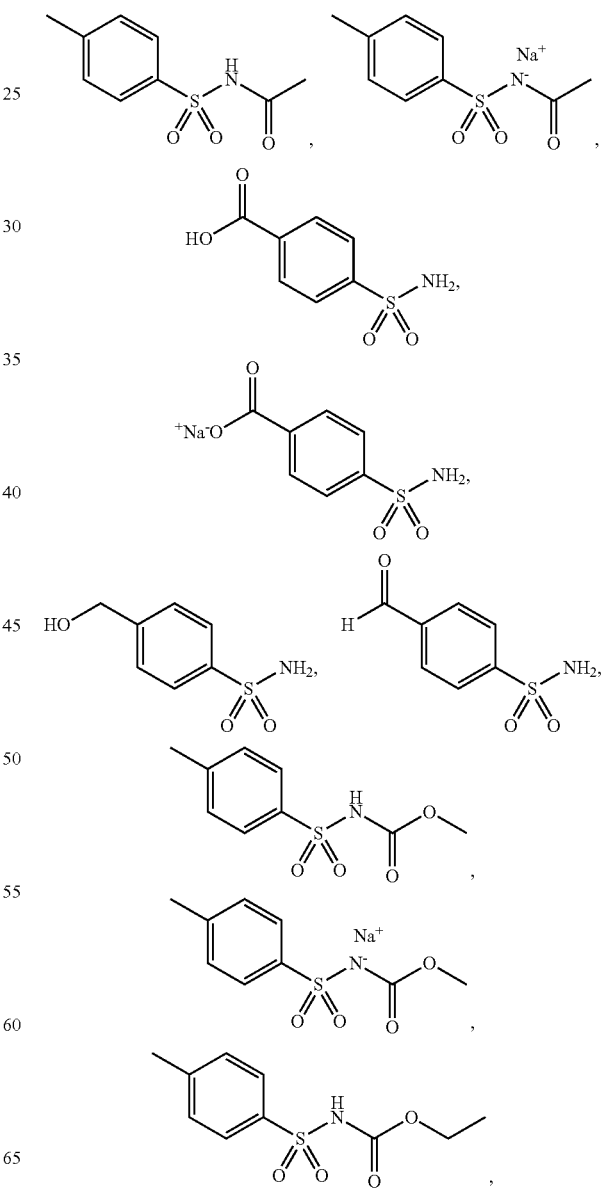

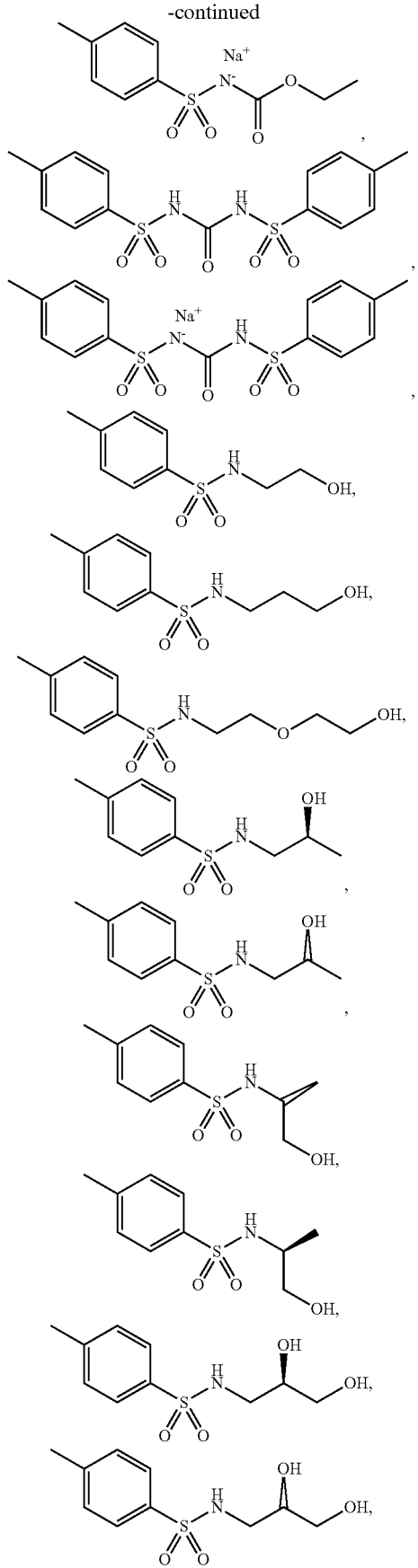
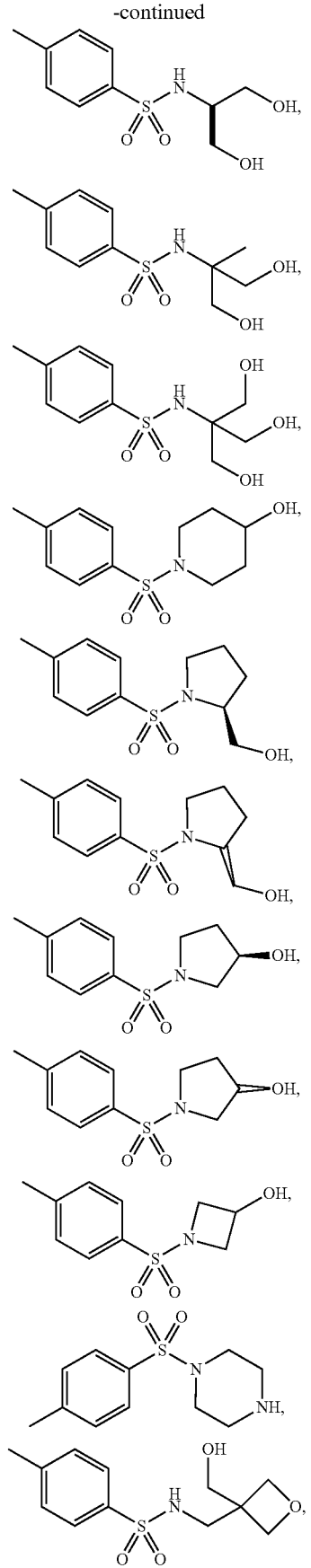

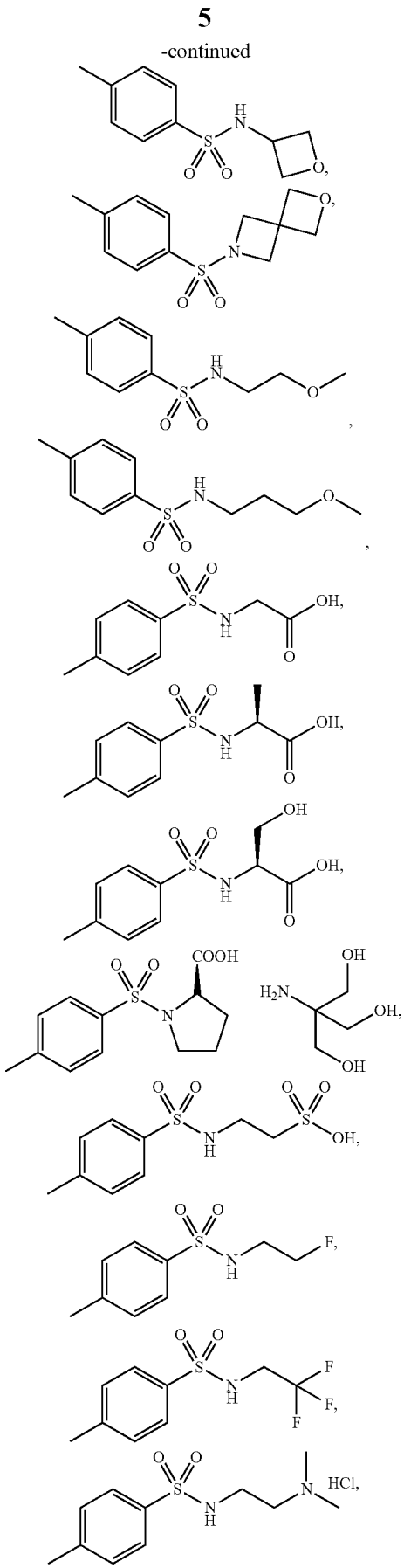

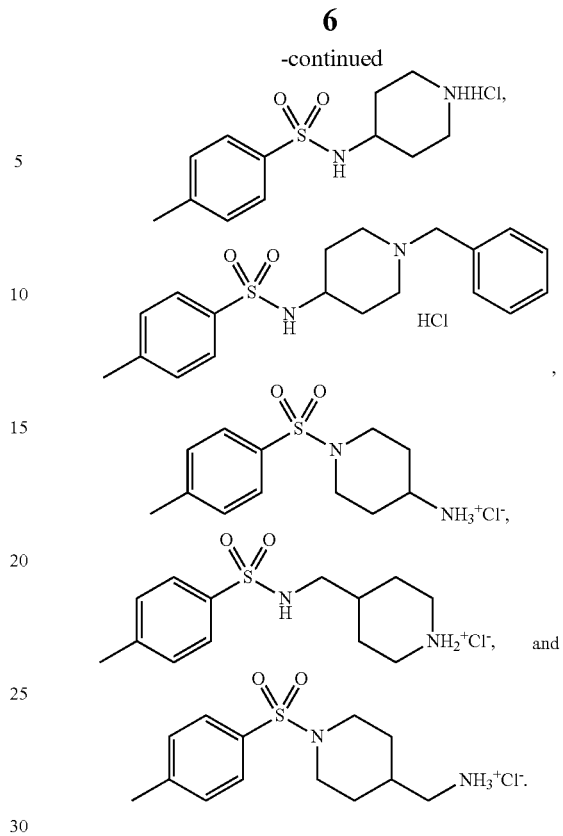

The present disclosure also provides a method for preventing or treating acne associated with *Propionibacterium acnes* and/or *Staphylococcus epidermis*, but not limited thereto, the method comprising applying the topical formulation to skin of a subject in need thereof. The present treatment is efficient and topical, and provides an anti-acne regimen that provides an effective treatment. It additionally provides less irritation compared with conventional therapies.

BRIEF DESCRIPTION OF THE DRAWINGS

The present disclosure can be more fully understood by reading the following detailed description of the embodiments, with reference made to the accompanying drawings, wherein:

FIGS. 2A to 2D show the antimicrobial activity of 4-fold test article dilution of the topical formulation of the present disclosure against *Staphylococcus epidermis*;

FIGS. 3A to 3D show the antimicrobial activity of 8-fold test article dilution of the topical formulation of the present disclosure against *Staphylococcus epidermis*;

FIGS. 4A to 4D show the antimicrobial activity of 16-fold test article dilution of the topical formulation of the present disclosure against *Staphylococcus epidermis*;

FIGS. 6A to 6D show the antimicrobial activity of 64-fold test article dilution of the topical formulation of the present disclosure against *Staphylococcus epidermis*;

DETAILED DESCRIPTION OF THE EMBODIMENTS

Figure 1:
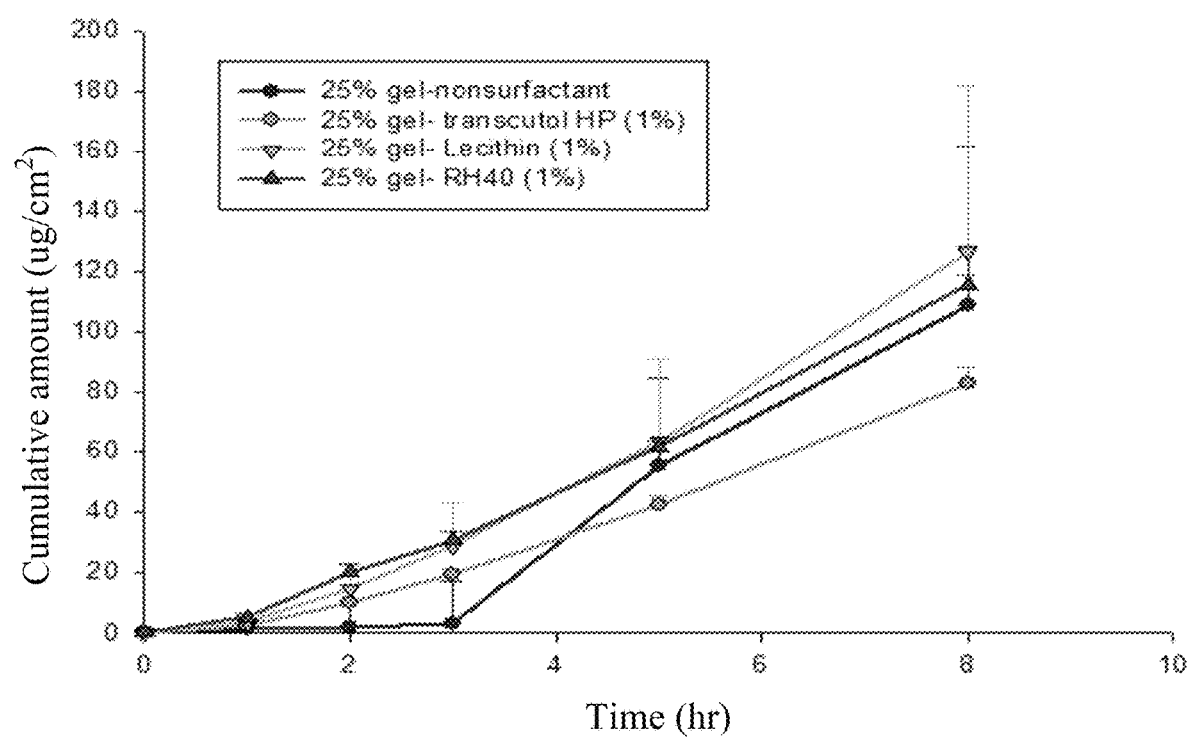
FIG. 1 shows a graph of a cumulative amount of p-TSA in the skin of nude mice after applying the p-TSA-containing topical formulation having 1% of various surfactants to the skin of nude mice.
Figure 5A:
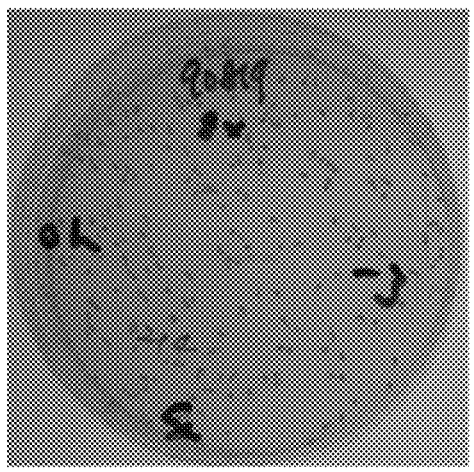
FIGS. 5A to 5D show the antimicrobial activity of 32-fold test article dilution of the topical formulation of the present disclosure against *Staphylococcus epidermis*.
Figure 5B:
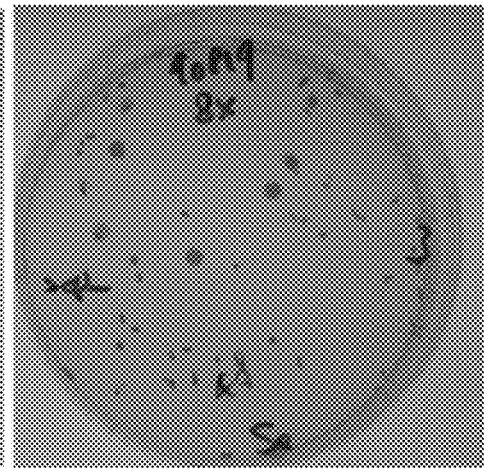
Figures 5C, 5D:
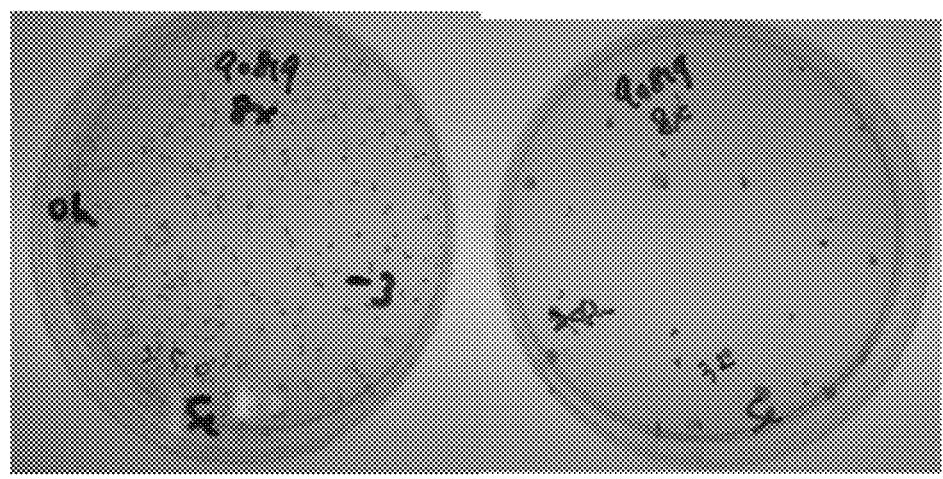

The following specific examples are used to exemplify the present disclosure. A person of ordinary skill in the art can conceive the other advantages of the present disclosure, based on the disclosure of the specification of the present disclosure. The present disclosure can also be implemented or applied as described in different specific examples. It is possible to modify and/or alter the above examples for carrying out this disclosure without contravening its spirit and scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a topical formulation for preventing or treating acne, comprising a benzenesulfonamide derivative, and a pharmaceutically or cosmetically acceptable excipient.

As used herein, the term "acne" refers to a skin disorder which causes by bacteria such as *Propionibacterium acnes* and *Staphylococcus epidermis*.

In one embodiment of the present disclosure, the benzenesulfonamide derivative is represented by formula (I):

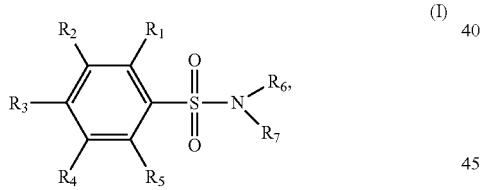

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In an embodiment of the present disclosure, the alkyl, alkoxy, cycloalkyl, cycloheteroalkyl and the ring in $R_1$ to $R_7$ are independently unsubstituted or substituted with one or more substituents. In another embodiment of the present disclosure, the substituent is selected from the group consisting of phenyl, halo, oxo, ether, hydroxyl, carboxyl, amino, sulfo and sulfonamide group.

In one embodiment of the present disclosure, the benzenesulfonamide derivative may include, but not limit to, para-toluenesulfonamide, ortho-toluenesulfonamide, meta-toluenesulfonamide, N-ethyl-para-toluene sulfonamide, N-ethyl-ortho-toluene sulfonamide, N-cyclohexyl-para-toluene sulfonamide,

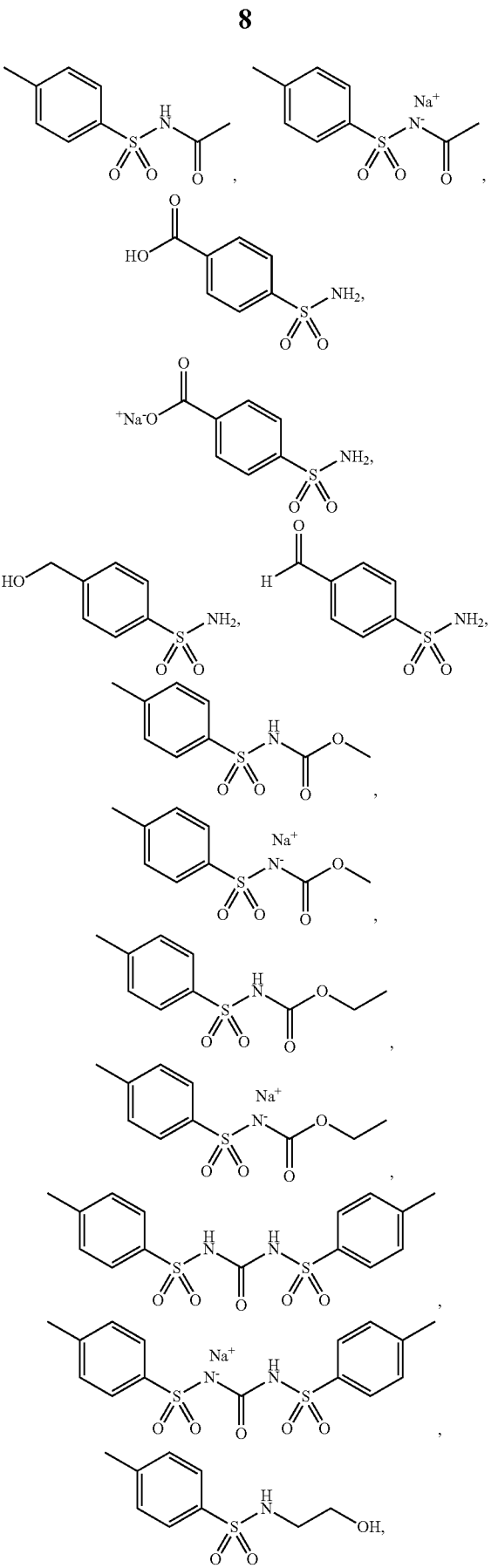

-continued
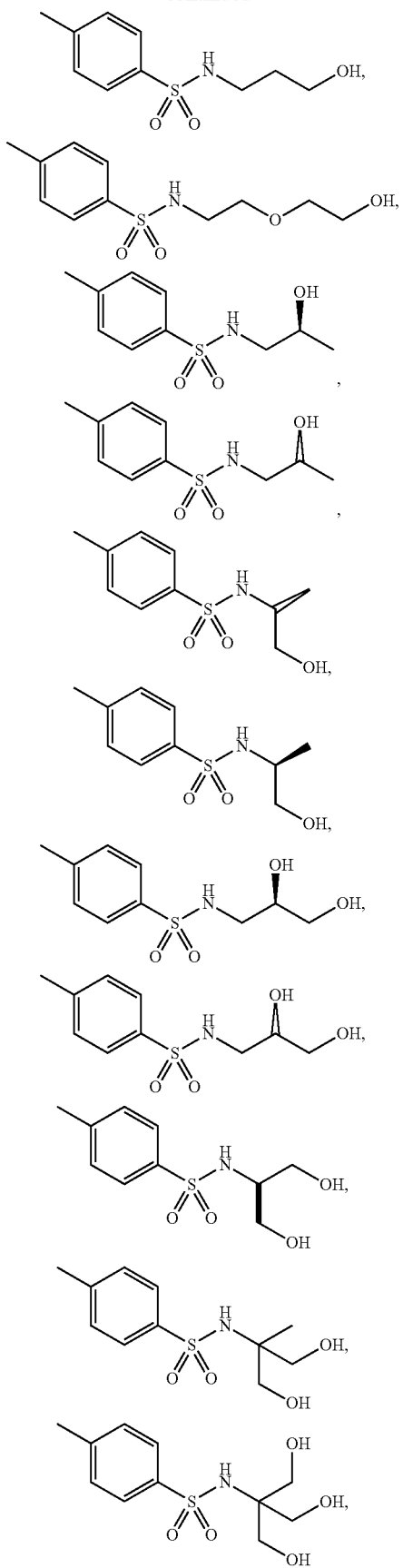
-continued
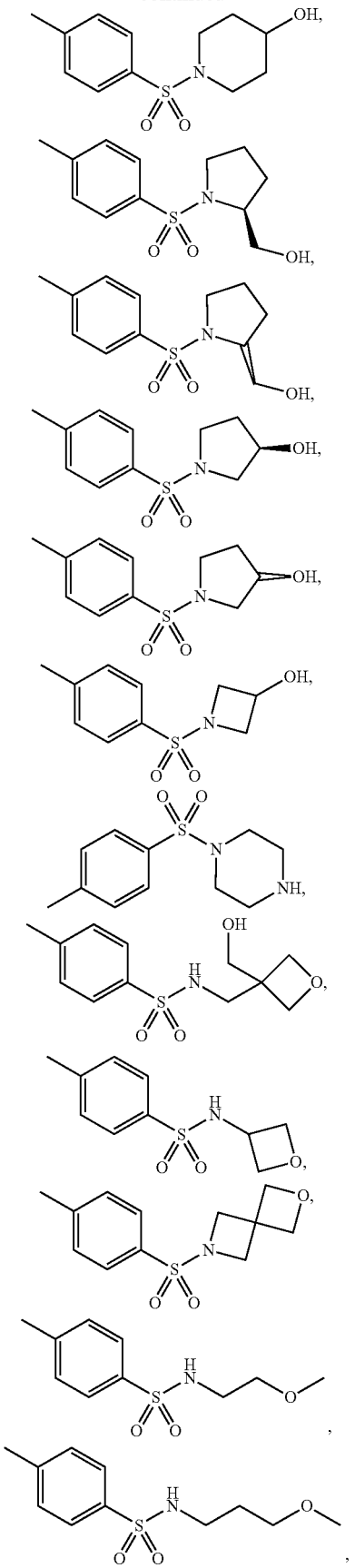

-continued

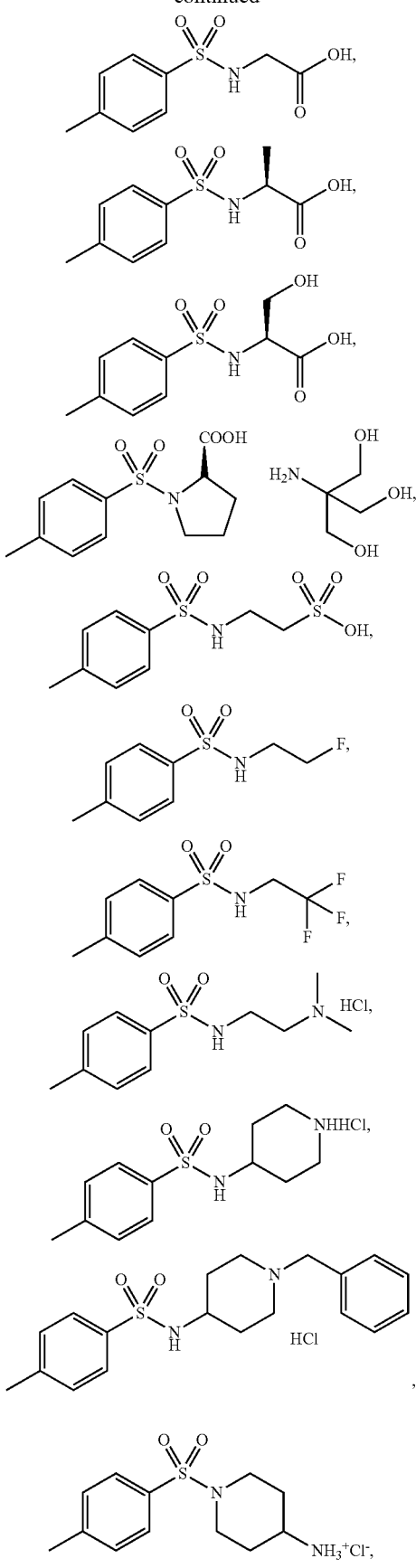

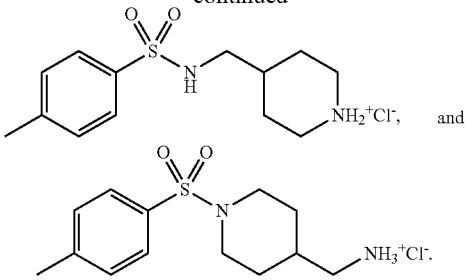

In one embodiment of the present disclosure, the pharmaceutically or cosmetically acceptable excipient may be a preservative, a lubricant, a suspending agent, a wetting agent, a flavoring agent, a thickening agent, a biocompatible solvent, a surfactant, a complexation agent, and any combination thereof.

In one embodiment of the present disclosure, the preservative may include, but not limit to, sodium benzoate, methyl paraben, propyl paraben, and cresols.

In one embodiment of the present disclosure, the lubricant may be metallic stearates which include, but is not limited to, magnesium, calcium and sodium stearates, stearic acid, talc, polyethylene glycols, and soluble salts. In another embodiment of the present disclosure, the salts include sodium chloride or sodium benzoate.

In one embodiment of the present disclosure, the wetting agent may include, but not limit to, glycerol, sorbitol, and polypropylene glycol.

In one embodiment of the present disclosure, the flavoring agents may include, but not limit to, peppermint oil, menthol, lemon oil, orange oil, and cinnamon oil.

In one embodiment of the present disclosure, the thickening agent may include, but not limit to, SEPINEO P600, SEPINEO DERM, CARBOPOL 980, sodium carboxymethyl cellulose (Na CMC), xanthan gum, hydroxypropyl cellulose (HPC), and polyvinylpyrrolidone K90 (PVP K90).

As used herein, the term "biocompatible" means generation of no significant undesirable host response for the intended utility. For example, biocompatible materials are non-toxic for the intended utility. Thus, for human utility, biocompatible is more preferably non-toxic to humans or human tissues.

In one embodiment of the present disclosure, the biocompatible solvent may be polyethylene glycol, propylene glycol, glycerol, sorbitol, ethanol, dimethyl sulfoxide, N-methyl-2-pyrrolidone (NMP), N,N-dimethylacetamide (DMA), glycofurol, acetone, isopropyl alcohol (IPA), triglyceride, benzyl benzoate, benzyl alcohol, solketal or any combination thereof.

In one embodiment of the present disclosure, the surfactant may be lecithin, macrogol 15 hydroxystearate, polyoxyethylene alkyl ether, polyoxyethylene castor oil, polyoxyethylene sorbitan fatty acid ester, polyoxyethylene stearate, polyoxylglyceride, sorbitan ester, tocopheryl polyethylene glycol succinate (TPGS) or any combination thereof.

In one embodiment of the present disclosure, the complexation agent may be polyvinyl pyrrolidone or cyclodextrin.

In one embodiment of the present disclosure, the benzenesulfonamide derivative is present in an amount ranging from about 1% to about 50% by weight. In another embodiment of the present disclosure, the benzenesulfonamide derivative is present in an amount ranging from about 5% to about 40% by weight. In another embodiment of the present disclosure, the benzenesulfonamide derivative is present in an amount ranging from about 10% to about 30% by weight. In still another embodiment of the present disclosure, the benzenesulfonamide derivative is present in an amount ranging from about 15% to about 25% by weight.

In one embodiment of the present disclosure, the pharmaceutically or cosmetically acceptable excipient is present in an amount ranging from about 30% to about 99% by weight. In another embodiment of the present disclosure, the pharmaceutically or cosmetically acceptable excipient is present in an amount ranging from about 40% to about 90% by weight. In another embodiment of the present disclosure, the pharmaceutically or cosmetically acceptable excipient is present in an amount ranging from about 50% to about 85% by weight. In still another embodiment of the present disclosure, the pharmaceutically or cosmetically acceptable excipient is present in an amount ranging from about 60% to about 75% by weight.

In one embodiment of the present disclosure, the topical formulation is in a non-aqueous form suitable for topical administration. In another embodiment of the present disclosure, the topical formulation may be in a form of a gel, a lotion, an ointment, an emulsifier, a paste or a cream.

In one embodiment of the present disclosure, the topical formulation is used as a pharmaceutical product or a cosmetic.

The present disclosure also provides a method for preventing or treating acne, comprising applying the topical formulation to the skin of a subject in need thereof. In one embodiment of the present disclosure, the benzenesulfonamide derivative in the topical formulation is applied in a dose effective to inhibit growth of an acne-causing bacterium.

In the treatment of acne, the topical formulation containing a benzenesulfonamide derivative is applied to an affected area, once or twice daily or as needed. In one embodiment of the present disclosure, the acne includes, but is not limited to, face acne, back acne or arm acne.

In one embodiment of the present disclosure, the topical formulation provides an antimicrobial activity against an acne-causing bacterium. In another embodiment of the present disclosure, the acne-causing bacterium includes *Propionibacterium acnes* and/or *Staphylococcus epidermis*.

The present disclosure also provides a method for sterilizing or inactivating an acne-causing bacterium on the skin of a subject in need thereof. In one embodiment of the present disclosure, the method comprises applying the topical formulation containing a benzenesulfonamide derivative to the skin of the subject, thereby preventing or treating acne on the skin of the subject.

The following are specific embodiments further demonstrating the efficacy of the current disclosure, but not to limit the scope of the current disclosure.

EXAMPLE

Example 1: Measuring Solubility of p-Toluenesulfonamide (p-TSA) in Various Solvents To screen the biocompatible solvents useful for preparation of the p-TSA-containing topical formulation, p-TSA was dissolved in various solvents at a maximum concentration. The results showed that dimethyl sulfoxide, polyethylene glycol 400 (PEG-400), glycofurol 75, propylene glycol, glycerol, absolute ethanol and 20% 7-sulfobutyl-ether-β-cyclodextrin were biocompatible solvents suitable for dissolving p-TSA. The solubility of p-TSA in such biocompatible solvents was shown in Table 1.

TABLE 1

Solubility of p-TSA in various solvents (n = 3)

| Solvents | Solubility (mg/mL) |
|---|---|
| Dimethyl sulfoxide (DMSO) | 785.95 |
| Polyethylene glycol 400 (PEG-400) | 466.52 |
| Glycofurol 75 | 443.13 |
| Propylene glycol (PG) | 117.86 |
| Glycerol | 28.42 |
| Absolute ethanol | 107.61 |
| 20% 7-sulfobutyl-ether-β-cyclodextrin (SBEβCD) | 17.59 |

Example 2: Development of p-TSA-Containing Topical Formulation

To develop a p-TSA-containing topical formulation in a gel form, 5%, 15% and 25% p-TSA were individually dissolved in 20%, 40% or 50% PEG-400 with 3% SEPINEO P600 as a thickening agent. The dissolution and precipitation behaviors of different batches of p-TSA-containing topical formulations were shown in Table 2. The results showed that 5% p-TSA could be completely dissolved in both 40% and 50% PEG-400 with 3% SEPINEO P600 (i.e., batches 5-1 and 5-2 in Table 2), and 15% and 25% p-TSA were merely dissolved completely in 50% PEG-400 with 3% SEPINEO P600 (i.e., batches 15-1 and 25-1 in Table 2). However, significant precipitation was found in batches 5-2, 15-1 and 25-2 of the topical formulations.

TABLE 2

Dissolution profiles of p-TSA in various solvents (n = 3)

| Components | Batch | | | | | | |
|---|---|---|---|---|---|---|---|
| | 5-1 | 5-2 | 15-1 | 15-2 | 25-1 | 25-2 | 25-3 |
| p-TSA | 5% | 5% | 15% | 15% | 25% | 25% | 25% |
| PEG-400 | 50% | 40% | 50% | 20% | 50% | 40% | 20% |
| SEPINEO P600 | 3% | 3% | 3% | 3% | 3% | 3% | 3% |
| H$_2$O | 42% | 52% | 32% | 62% | 22% | 32% | 52% |
| Dissolution behavior | Dissolved | Dissolved | Dissolved | Incompletely dissolved | Dissolved | Incompletely dissolved | Incompletely dissolved |
| Precipitation * | N.D. | Significant | Significant | N.D. | Significant | N.D. | N.D. |

1. * Drug precipitation within the topical formulation was examined by use of a light microscope.
2. N.D. is defined as not determined.
3. % means the percentage by weight.

To further examine the characterization of p-TSA gel, 25% p-TSA dissolved in 62% PEG-400 with various thickening agents, including SEPINEO P600, SEPINEO DERM, CARBOPOL 980, sodium carboxymethyl cellulose (Na CMC), xanthan gum, hydroxypropyl cellulose (HPC) and polyvinylpyrrolidone K90 (PVP K90) were prepared. The sample appearance and precipitation behavior of the p-TSA gels were observed, and the results were shown in Table 3. The results showed that stable topical formulation in gel form was successfully manufactured by dissolving 25% p-TSA in 62% PEG-400 with 3% SEPINEO P600 or 3% SEPINEO DERM (batches 25-5 and 25-6).

1% Kolliphor RH40 and 10% $H_2O$ was prepared for the test of antimicrobial activity analysis against *Staphylococcus epidermis*. The minimum inhibitory concentration test (MIC test) was performed by reference to the turbidimetric assay described in Antibiotics-Microbial Assays of US Pharmacopeia. Briefly, the procedures of MIC test in this example were described as follows:

(1) 5 g GW-5201 (hereafter also referred to as "test article") was added in 15 mL 25% DMSO as being a 4-fold test article dilution, and additional serial dilution was performed to obtain 8-fold, 16-fold, 32-fold and 64-fold test article dilutions.

TABLE 3

Characterization of p-TSA-containing topical formulations having various thickening agents

| Components | 25-5 | 25-6 | 25-7 | 25-8 | 25-9 | 25-10 | 25-11 |
|---|---|---|---|---|---|---|---|
| p-TSA | 25% | 25% | 25% | 25% | 25% | 25% | 25% |
| PEG-400 | 62% | 62% | 62% | 62% | 62% | 62% | 62% |
| Thickening agent | 3% SEPINEO P600 | 3% SEPINEO DERM | 3% CARBOPOL 980 | 3% Na CMC | 3% Xanthan gum | 3% HPC | 3% PVP K90 |
| $H_2O$ | 10% | 10% | 10% | 10% | 10% | 10% | 10% |
| Appearance | Translucent gel | Translucent gel | Translucent gel, but few white powder clumps exists | Opaque suspension, sediment occurred after sample standing for a while | Opaque suspension, sediment occurred after sample standing for a while | Highly viscous solution, with presence of transparent gel-like stuffs | Transparent, viscous solution |
| Precipitation * | No | No | No | Substantial | Substantial | No | No |

1. * Drug precipitation within the topical formulation was examined by use of a light microscope.
2. % means the percentage by weight.

Example 3: Penetrability of p-TSA-Containing Topical Formulation

To examine the penetration effect of a p-TSA-containing topical formulation in the gel form, 25% p-TSA was dissolved in 62% PEG-400 with 1% of various surfactants, including Transcutol HP, lecithin and Kolliphor RH40 (BASF Corporation) as shown in Table 4.

TABLE 4

Components of p-TSA-containing topical formulations having various surfactants

| Components | Sample 1 | Sample 2 | Sample 3 | Sample 4 |
|---|---|---|---|---|
| p-TSA | 25% | 25% | 25% | 25% |
| PEG-400 | 62% | 62% | 62% | 62% |
| Surfactant | — | 1% Transcutol HP | 1% lecithin | 1% Kolliphor RH40 |
| $H_2O$ | 13% | 12% | 12% | 12% |

Further, 10 mg of each of Samples 1-4 was respectively applied to 1 $cm^2$ area of the skin of nude mice, followed by measuring the cumulative amount of p-TSA by HPLC. Referring to FIG. 1, the results showed that the surfactants, especially lecithin, rendered the penetrability to p-TSA topical formulation.

Example 4: Antimicrobial Activity of p-TSA-Containing Topical Formulation (GW-5201)

p-TSA-containing topical formulation (GW-5201) consisting of 25% p-TSA, 61% PEG-400, 3% SEPINEO P600, (2) A pure culture of *Straphyulococcus epidermis* (BCRC 17069) was diluted with Dulbecco's phosphate buffered saline (Sigma, Cat No. D5652) to achieve a target challenge of $1 \times 10^7$ to $1 \times 10^8$ CFU/mL.

(3) 100 μL of $1 \times 10^7$ to $1 \times 10^8$ CFU/mL test inoculums suspension was added into 10 mL 4-fold, 8-fold, 16-fold, 32-fold and 64-fold test article dilution, respectively, to achieve the final concentration of $1 \times 10^5$ to $1 \times 10^6$ CFU/mL. Each of the inoculated 4-fold, 8-fold, 16-fold, 32-fold and 64-fold test article dilutions was incubated at 20° C. to 25° C. for 24 hours.

(4) After 24 hours incubation, 1 mL aliquot of each test article dilution was withdrawn, and respectively added to individual tubes containing 9 mL of Modified Letheen Broth (MLB) (BD, REF: 263010). The samples in each MLB were then 10-fold serially diluted and vortexed for 2 minutes. Further, 1 mL of diluted samples from 4-fold, 8-fold, 16-fold, 32-fold and 64-fold test article dilutions were respectively transferred into sterile petri-dish.

(5) Each of the bacterial recovery plates was incubated at 30° C. to 35° C. for 2 to 4 days, and then enumerated for viable counts.

(6) The antimicrobial activity (log reduction, R) against bacteria was calculated by the formula of R=log B−log A, wherein R represented the value of antimicrobial activity; A represented average of the number of viable counts from the test inoculums; and B represented average of the number of viable counts from the inoculated sample after 24 hours.

FIGS. 2A-2D, 3A-3D, 4A-4D, 5A-5D and 6A-6D respectively represented the bacterial recovery plates treated with 4-fold, 8-fold, 16-fold, 32-fold and 64-fold test article dilutions of two individual samples (Group 1 and Group 2) for 0 hour or 24 hours and the bacterial contents and antimicrobial activity in each plate were shown in Table 5. The results showed that after 24 hours incubation, 4-fold, 8-fold, 16-fold and 32-fold test article dilutions all revealed 3 log reduction of S. epidermis. Therefore, the minimum inhibitory concentration of p-TSA-containing topical formulation (GW-S201) was defined as 32-fold.

TABLE 5

| The bacterial contents and antimicrobial activity (R) | | | | | |
|---|---|---|---|---|---|
| Test Article No. | | | UB90819 | | |
| Test train | | | S. epidermis | | |
| Dilution fold | 4 | 8 | 16 | 32 | 64 |
| Inoculum, A (CFU/mL) | $2.44 \times 10^5$ | $2.48 \times 10^5$ | $2.43 \times 10^5$ | $2.32 \times 10^5$ | $2.55 \times 10^5$ |
| log A | 5.39 | 5.39 | 5.39 | 5.37 | 5.41 |
| Inoculated sample after 24 hours, B (CFU/mL) | <1* | <1* | <1* | $4.00 \times 10^1$ | $1.46 \times 10^5$ |
| log B | <0 | <0 | <0 | 1.60 | 5.16 |
| R | >5.39 | >5.39 | >5.39 | 3.77 | 0.25 |

<1*: There is no obvious colony formation on the culture plate.

By using the protocol described or similarly described in this example, the topical formulation of the present disclosure was demonstrated to have antimicrobial activity against Propionibacterium acnes, but data are not shown.

Example 5: Treatment of Acne by Use of p-TSA-Containing Topical Formulation (GW-S201)

Figure 7A:
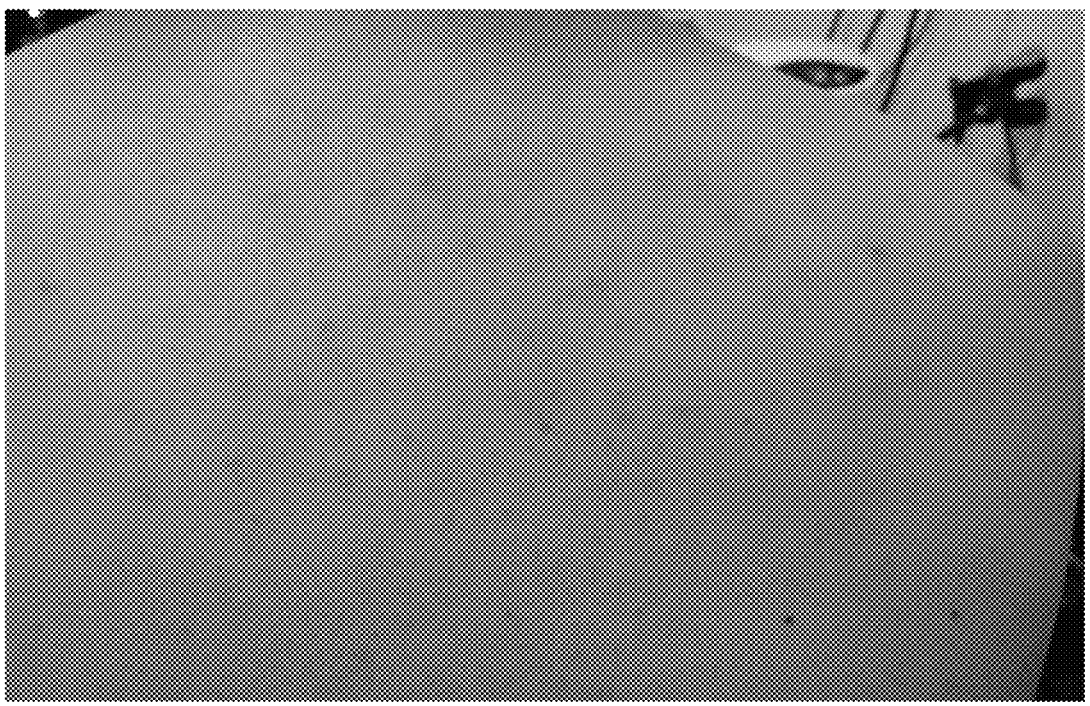
FIGS. 7A and 7B show the back of a subject before and after the treatment of the p-TSA-containing topical formulation (GW-S201)
Figure 7B:

Clinical Case I:
As shown in FIG. 7A, a subject was suffering from back acne, and FIG. 7B showed that the severity of back acne had been reduced obviously after applying the p-TSA-containing topical formulation (GW-S201) evenly to the subject's back skin for three or four times a day within one week. In addition, GW-S201 did not cause skin irritation.

Figure 8A:
FIGS. 8A and 8B show the face (forehead) of a subject before and after the treatment of the p-TSA-containing topical formulation (GW-S201)
Figure 8B:

Clinical Case II:
As shown in FIG. 8A, a subject was suffering from face acne, and FIG. 8B showed that the face acne was improved after applying the p-TSA-containing topical formulation (GW-S201) evenly to the subject's face for three or four times a day within one week. In addition, GW-S201 did not cause skin irritation.

Figure 9A:
FIGS. 9A and 9B show the face of another subject before and after the treatment of the p-TSA-containing topical formulation (GW-S201)
Figure 9B:

Clinical Case III:
As shown in FIG. 9A, a subject was suffering from face acne, and FIG. 9B showed that the face acne was improved after applying the p-TSA-containing topical formulation (GW-S201) evenly to the subject's face for three or four times a day within 3 days. In addition, GW-S201 did not cause skin irritation.

Figure 10A:
FIGS. 10A and 10B show the arm of a subject before and after the treatment of the p-TSA-containing topical formulation (GW-S201).
Figure 10B:
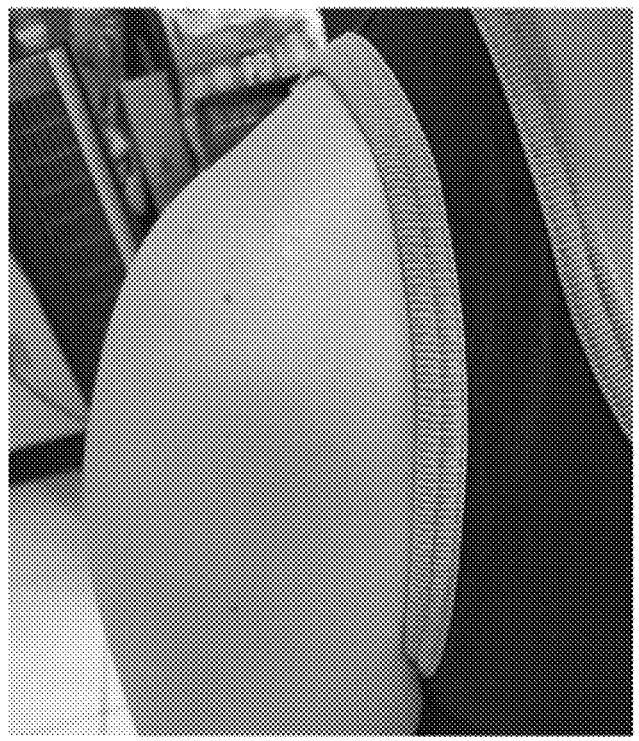

Clinical Case IV:
As shown in FIG. 10A, a subject was suffering from arm acne, and FIG. 10B showed that the arm acne was disappeared after applying the p-TSA-containing topical formulation (GW-S201) evenly to the subject's arm skin for three or four times a day within one week. In addition, GW-S201 did not cause skin irritation.

From the above clinical cases I to IV, it was clearly showed that p-TSA-containing topical formulation (GW-S201) efficiently treated acne, including back acne, face acne and arm acne in a subject without causing skin irritation.

The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A method for treating acne, comprising applying a topical formulation comprising a benzenesulfonamide derivative to skin of a subject in need thereof, wherein the benzenesulfonamide derivative in the topical formulation is applied in a dose effective to inhibit growth of an acne-causing bacterium, wherein the benzenesulfonamide derivative is at least one selected from the group consisting of para-toluene sulfonamide, ortho-toluene sulfonamide, meta-toluene sulfonamide, N-ethyl-para-toluene sulfonamide, N-ethyl-ortho-toluene sulfonamide, N-cyclohexyl-para-toluene sulfonamide,

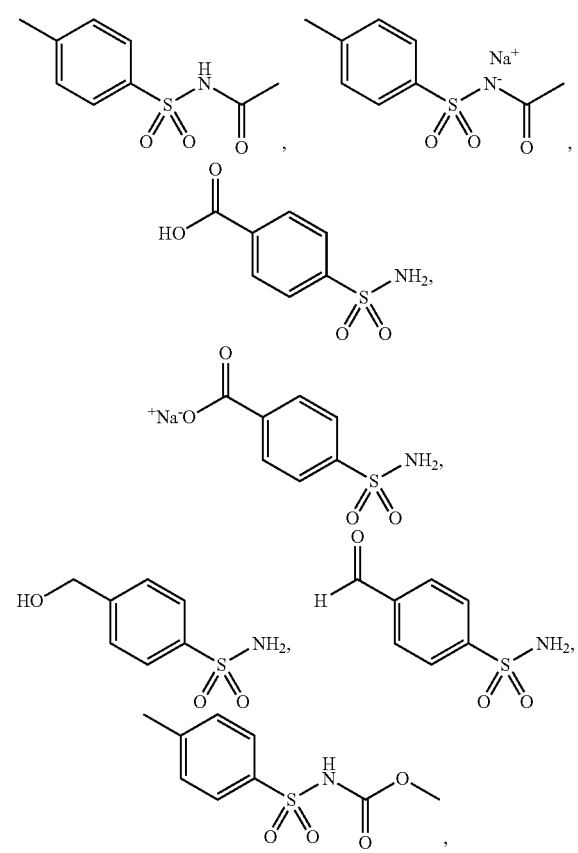

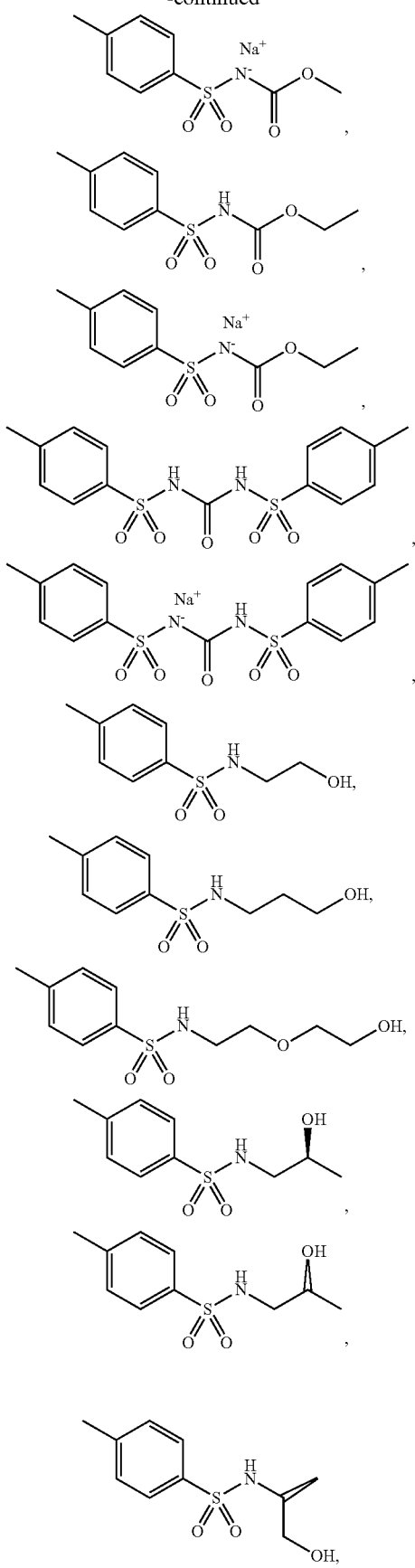
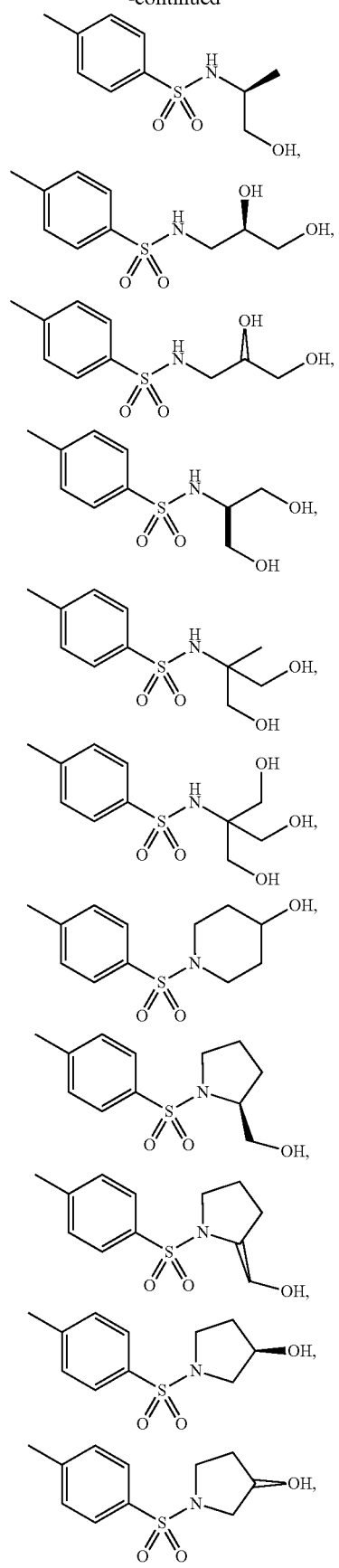

-continued

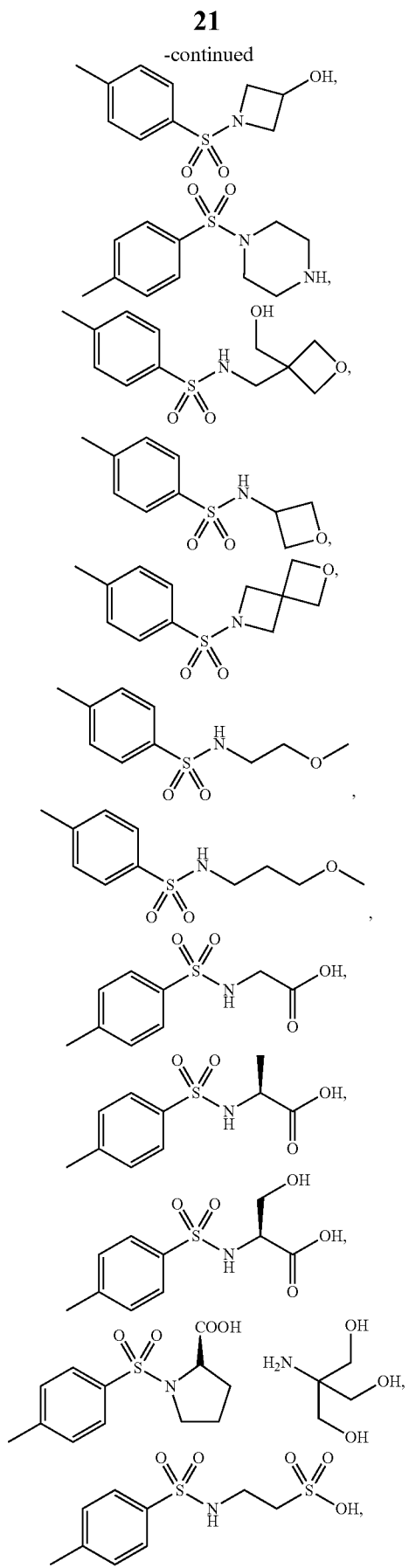

-continued

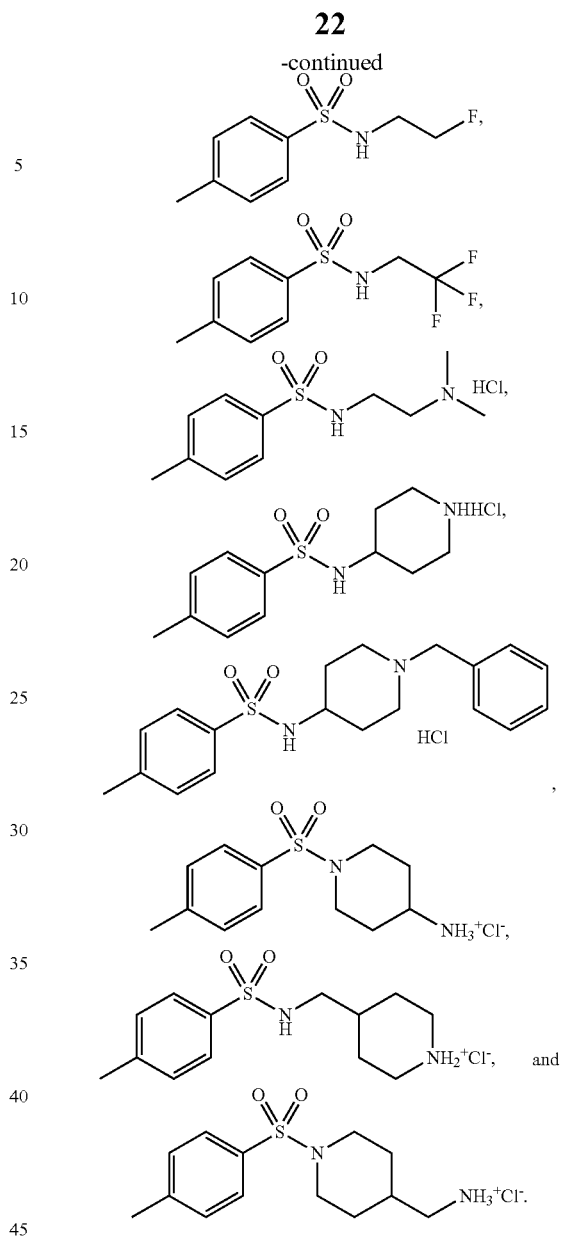

2. The method according to claim 1, wherein the benzenesulfonamide derivative in the topical formulation is applied to the skin of the subject in a therapeutically effective amount of from about 1% to about 50% by weight.

3. The method according to claim 1, wherein the benzenesulfonamide derivative in the topical formulation is applied to the skin of the subject in a therapeutically effective amount of from about 5% to about 40% by weight.

4. The method according to claim 1, wherein the benzenesulfonamide derivative in the topical formulation is applied to the skin of the subject in a therapeutically effective amount of from about 15% to about 30% by weight.

5. A method for sterilizing or inactivating an acne-causing bacterium on skin of a subject in need thereof, comprising applying the topical formulation according to claim 1 to the skin of the subject, thereby treating acne on the skin of the subject.

6. The method according to claim 5, wherein the acne-causing bacterium is at least one of *Propionibacterium acnes* and *Staphylococcus epidermis*.

7. The method according to claim 1, wherein the topical formulation comprises a pharmaceutically or cosmetically acceptable excipient that is at least one selected from the group consisting of a preservative, a lubricant, a suspending agent, a wetting agent, a flavoring agent, a thickening agent, a biocompatible solvent, a surfactant, a complexation agent, and any combination thereof.

8. The method according to claim 7, wherein the biocompatible solvent is at least one selected from the group consisting of polyethylene glycol, propylene glycol, glycerol, sorbitol, ethanol, dimethyl sulfoxide, N-methyl-2-pyrrolidone, N,N-dimethylacetamide, glycofurol, acetone, isopropyl alcohol, triglyceride, benzyl benzoate, benzyl alcohol, solketal and any combination thereof.

9. The method according to claim 7, wherein the surfactant is at least one selected from the group consisting of lecithin, macrogol 15 hydroxystearate, polyoxyethylene alkyl ether, polyoxyethylene castor oil, polyoxyethylene sorbitan fatty acid ester, polyoxyethylene stearate, polyoxylglyceride, sorbitan ester, tocopheryl polyethylene glycol succinate, polyoxyl castor oil and any combination thereof.

10. The method according to claim 7, wherein the complexation agent is at least one of polyvinyl pyrrolidone and cyclodextrin.

\* \* \* \* \*